US011382563B2

(12) United States Patent
Cates et al.

(10) Patent No.: US 11,382,563 B2
(45) Date of Patent: Jul. 12, 2022

(54) SYSTEM AND METHOD FOR DETECTING VENTILATORY DEPRESSION AND FOR PROMPTING A PATIENT TO BREATHE

(71) Applicant: Respiration AI, LLC, West Valley City, UT (US)

(72) Inventors: Lara M. Brewer Cates, Salt Lake City, UT (US); Kenward B. Johnson, Sandy, UT (US); Joseph A. Orr, Park City, UT (US); Talmage Egan, Holladay, UT (US); Soeren Hoehne, Salt Lake City, UT (US); Noah Syroid, Salt Lake City, UT (US)

(73) Assignee: RESPIRATION AI, LLC, Salt Lake City, UT (US)

( * ) Notice: Subject to any disclaimer, the term of this patent is extended or adjusted under 35 U.S.C. 154(b) by 600 days.

(21) Appl. No.: 16/290,812

(22) Filed: Mar. 1, 2019

(65) Prior Publication Data
US 2020/0275882 A1 Sep. 3, 2020

(51) Int. Cl.
*A61B 5/00* (2006.01)
*A61B 5/0205* (2006.01)
(Continued)

(52) U.S. Cl.
CPC .......... *A61B 5/486* (2013.01); *A61B 5/02055* (2013.01); *A61B 5/721* (2013.01); *A61B 5/7282* (2013.01); *A61B 5/7405* (2013.01); *A61B 5/7425* (2013.01); *A61B 5/7455* (2013.01); *A61B 5/02416* (2013.01); *A61B 5/038* (2013.01); *A61B 5/05* (2013.01);
(Continued)

(58) Field of Classification Search
CPC ... A61B 5/486; A61B 5/02055; A61B 5/7282; A61B 5/7405; A61B 5/7425; A61B 5/7455; A61B 5/02416; A61B 5/038; A61B 5/05; A61B 5/0809; A61B 5/0826; A61B 5/0836; A61B 5/11; A61B 5/14542; A61B 5/4818; A61B 7/003; A61B 2562/0219; A61B 2562/029
USPC ........................................................ 600/301
See application file for complete search history.

(56) References Cited

U.S. PATENT DOCUMENTS 3,802,417 A 4/1974 Lang
3,882,847 A 5/1975 Jacobs
(Continued)

FOREIGN PATENT DOCUMENTS

EP 0890369 4/2000
WO WO2009050702 4/2009
(Continued)

*Primary Examiner* — Aaron F Roane
(74) *Attorney, Agent, or Firm* — Morriss O'Bryant Compagni Cannon, PLLC

(57) ABSTRACT

A system and method for prompting a patient experiencing ventilatory depression to breathe includes at least one sensor for detecting ventilatory depression by detecting inadequate breathing or lack of breathing in the patient. The system also includes one or more sensors for determining the type of breathing problem experienced by the patient. A sensor for detecting motion of the patient is used to determine whether the patient is moving. If inadequate or a lack of breathing is detected and the patient is not moving, the system provides verbal prompts or tactile stimuli to prompt the patient to breathe to improve patient ventilation.

28 Claims, 11 Drawing Sheets

(51) Int. Cl.
  *A61B 5/024* (2006.01)
  *A61B 5/03* (2006.01)
  *A61B 5/083* (2006.01)
  *A61B 5/05* (2021.01)
  *A61B 5/08* (2006.01)
  *A61B 7/00* (2006.01)
  *A61B 5/145* (2006.01)
  *A61B 5/11* (2006.01)

(52) U.S. Cl.
  CPC .......... *A61B 5/0809* (2013.01); *A61B 5/0826* (2013.01); *A61B 5/0836* (2013.01); *A61B 5/11* (2013.01); *A61B 5/14542* (2013.01); *A61B 5/4818* (2013.01); *A61B 7/003* (2013.01); *A61B 2562/029* (2013.01); *A61B 2562/0219* (2013.01)

(56) References Cited

U.S. PATENT DOCUMENTS

| | | | |
|---|---|---|---|
| 3,950,799 | A | 4/1976 | Frank |
| 4,694,839 | A | 9/1987 | Timme |
| 4,803,471 | A | 2/1989 | Rowland |
| 5,178,156 | A | 1/1993 | Takishima et al. |
| 5,534,851 | A | 7/1996 | Russek |
| 5,555,891 | A | 9/1996 | Eisenfeld |
| 5,836,302 | A | 11/1998 | Homuth et al. |
| 6,305,373 | B1 | 10/2001 | Wallace et al. |
| 6,454,724 | B1 | 9/2002 | Greene |
| 7,025,730 | B2 | 4/2006 | Cho et al. |
| 7,034,692 | B2 | 4/2006 | Hickle |
| 7,115,097 | B2 | 10/2006 | Johnson |
| 7,327,219 | B2 | 2/2008 | Lederer, IV |
| 8,226,570 | B2 | 7/2012 | Pu et al. |
| 8,348,941 | B2 | 1/2013 | Tehrani |
| 8,378,832 | B2 | 2/2013 | Cassidy |
| 8,467,876 | B2 | 6/2013 | Tehrani |
| 8,603,010 | B2 | 12/2013 | Lange et al. |
| 8,744,779 | B2 | 6/2014 | Syroid et al. |
| 8,838,245 | B2 | 9/2014 | Lin et al. |
| 9,381,314 | B2 | 7/2016 | Thiessen |
| 9,883,809 | B2 | 2/2018 | Klap et al. |
| 9,901,261 | B2 | 2/2018 | McCombie et al. |
| 2005/0197588 | A1 | 9/2005 | Freeberg |
| 2006/0097879 | A1* | 5/2006 | Lippincott .............. G16H 50/20 340/573.1 |
| 2007/0208232 | A1 | 9/2007 | Kovacs |
| 2008/0071185 | A1 | 3/2008 | Beck et al. |
| 2009/0099621 | A1 | 4/2009 | Lin et al. |
| 2011/0032103 | A1* | 2/2011 | Bhat ..................... G08B 25/10 340/573.1 |
| 2013/0331662 | A1 | 12/2013 | Stoian et al. |
| 2014/0005502 | A1 | 1/2014 | Klap et al. |
| 2014/0012099 | A1 | 1/2014 | Halperin et al. |
| 2014/0230818 | A1 | 8/2014 | Jafari et al. |
| 2014/0230819 | A1 | 8/2014 | Rawlins et al. |
| 2015/0190088 | A1* | 7/2015 | Chen .................. A61B 5/02055 600/301 |
| 2018/0005505 | A1 | 1/2018 | Goodson |
| 2020/0297955 | A1* | 9/2020 | Shouldice .............. G16H 40/67 |

FOREIGN PATENT DOCUMENTS

| | | |
|---|---|---|
| WO | WO2016196837 | 12/2016 |
| WO | WO2017088339 | 6/2017 |

* cited by examiner

SYSTEM AND METHOD FOR DETECTING VENTILATORY DEPRESSION AND FOR PROMPTING A PATIENT TO BREATHE

BACKGROUND

Field of the Invention

The present invention relates generally to systems for detecting ventilatory depression of a patient, and more specifically to a systems and method for providing patient stimulus when ventilatory depression is detected in a patient.

State of the Prior Art

Opioid-induced ventilatory depression is a well-known cause of morbidity and mortality during postoperative periods. The underlying cause in two of every three unexpected hospital deaths is hypoventilation. Drugs given after surgery to control pain lower the patient's respiratory drive, and the effort becomes inadequate to remove sufficient carbon dioxide. As the concentration of CO2 in the patient's arterial blood rises and the $O_2$ falls, the patient becomes increasingly susceptible to abnormal cardiac rhythms and, ultimately, to cardiac arrest and death. The American Society of Anesthesiologists Task Force on Sedation and Analgesia identified drug-induced hypoventilation and airway obstruction as the primary cause of morbidity associated with sedation and analgesia. In a 2015 analysis of the Anesthesia Closed Claims Project database, Lee, et al. concluded that 97% of deaths and injuries resulting from opioid-induced hypoventilation could have been prevented with better monitoring and clinician response.

Experts and consensus guidelines recommend that patients receiving postoperative analgesia be continuously monitored for respiratory rate. A number of measures have been studies to monitor patient condition during postoperative periods to detect respiratory rates in non-intubated subjects including using sensors to measure airflow, to measure chest wall movement, and/or to measure expired gas of the patient. Despite such studies, no sensor has emerged as a standard for monitoring respiratory rate of a patient in postoperative care, especially for non-intubated patients and low respiratory rates. In addition, differences in the studied patient populations, reference signals, respiratory rate detection and the statistical models used in the studies make comparisons between such studies difficult.

A further challenge for patient safety is that there are settings in which patients may not be adequately monitored to be able to detect a lack of adequate ventilation. For example, ventilation of patients in general wards or outpatient settings may not be monitored. When inadequate ventilation persists for a sufficient period of time, a patient may die or experience severe morbidity. Prior art patient monitoring systems often measure breath rate (number of breaths in a minute or an averaging period) or tidal volume per breath.

Traditional patient monitoring systems aim to read the measured values even in the presence of patient motion. Such patient monitoring systems rely on a pulse oximeter to alarm when a patient stops breathing. When breathing effort becomes weak or stops, the oxygen stores in the patient's lungs will eventually become depleted, the patient will become hypoxic and the pulse oximeter will alarm. Respiratory arrest usually progresses to cardiopulmonary arrest within 10 minutes. The pulse oximeter measures the blood oxygen saturation ($SpO_2$), but it is a delayed indicator of ventilation problems. When the oxygen saturation drops below 90%, the monitor sounds a low $SpO_2$ alarm. This alarm requires the busy clinician to stop what he or she is doing, go to the patient's room, and verify the patient is breathing adequately. Unfortunately, delayed interventions occur in 50% of patients with respiratory distress, with a median delay duration of 12 hours, and inadequate nursing assessments/response have been implicated in a third of deaths from hypoventilation. In a closed claims database analysis, the time between the last nursing check and the discovery of a patient with hypoventilation injury or death was within 2 hours in 42% and within 15 minutes in 16% of cases. Therefore, a system must act quickly to prevent injury and save a patient's life. Artifacts from hand motion such as when the patient eats, adjusts their blanket or any myriad of minor activities, also cause the pulse oximeter to produce false alarms regularly. These frequent pulse oximeter false alarms are a significant source of alarm fatigue and increased workload for clinicians and can delay necessary patient care for patients in urgent need of help. In some cases, the patient is safe while the nurse is in the room prompting for breaths, but returns to an unsafe status once left unattended.

Each year, 41 million non-cardiac inpatient surgeries are performed in the U.S., and most of the patients stay in general hospital wards until discharge. Inpatients with hypoventilation originating on the general care floor had higher mortality rates (34.6%) than non-hypoventilation cases (1.2%) and longer lengths of hospital and ICU stays (11.5, 5.8 days) than non-hypoventilation cases (4.1, 2.9 days). Up to 85% of post-surgical mortalities occur on the general ward, where patient monitoring is often inadequate and nursing time with each patient is limited. While it is known that the underlying cause in two of every three unexpected hospital deaths is hypoventilation, and despite a recommendation from the Anesthesia Patient Safety Foundation to use continuous monitoring of both oxygenation (pulse oximetry) and ventilation in patients receiving opioids in the postoperative period, many general ward patients' $SpO_2$ and respiratory rate are only spot-checked once every four hours. Hypoventilation occurs because the sedation and pain medication given to the patients may relax them so deeply that they stop breathing unless prompted. Although patients with pain medication are likely to have respiration problems, respiratory rate is the least commonly documented vital sign. Emerging hypoventilation can lead to death within a few minutes or it may take over an hour depending on the severity, rate of onset and baseline health of the patient. When the nurse stimulates the patient by entering the room to visually observe respiratory rate and spot check $SpO_2$, the vital signs are not indicative of the patient's unstimulated state. Furthermore, checking on the patient only once every four hours leaves the patient at significant risk for deterioration while left unattended. Given the nurses' heavy work burden and the propensity for many false alarms on existing $SpO_2$ monitors, patients often deteriorate without notice.

Many patient deaths and cases of morbidity are preventable if respiratory problems are detected early and the patient is wakened and prompted to breathe. Thus, an automated system that both reliably detects the problem early and directly prompts the patient to breathe provides a fundamental change in the management of high-risk patients that could reduce the number of unexpected hospital deaths while reducing nurse workload caused by frequent false positive $SpO_2$ alarms. As set forth herein, the present invention provides a ventilation prompting system that encourages a patient to self-rescue until a nurse or other caregiver can be summoned to the bedside.

SUMMARY OF THE INVENTION

Accordingly, the present invention provides a system for detecting breathing of a patient and for providing an alert when an abnormal breathing condition is detected in the patient. The present invention provides universal, continuous surveillance with one or more ventilation monitors in place of spot-checking, such as during a post-operative period, to reduce the number of rescue events to restore ventilation and reduce the number emergency transfers to an ICU to manage adverse respiratory events. The present invention includes continuous ventilation, movement and SpO2 monitoring to determine if the patient is being adequately ventilated and a system to prompt the patient to breathe if ventilation is inadequate to improve patient safety. At least one sensor or a plurality of sensors quickly identifies hypoventilation and rejects false positive alarms. The sensor or sensors may include capnography or other sensors to monitor ventilation and one or more motion sensors paired with pulse oximetry to identify when a finger or other body part of the patient is moving, in order to reject motion artifacts to provide reliable blood oxygenation measurements. The system of the present invention includes systems and devices that combine improved $SpO_2$ monitoring with respiratory rate monitoring to make the detection of hypoventilation significantly more reliable thereby reducing the occurrence of false alarms.

The present invention not only improves the monitoring capability of patient ventilation and ventilation conditions, the present invention provides systems of improving alert and response times when a patient ventilation problem has been detected. The present invention provides an automated, and integrated system that directly prompts the patient to breathe until help can be summoned to assist the patient. The present invention sets forth the level and type of prompting needed to persuade a patient to breathe in spite of administration of sedatives, opioid analgesics, non-opioid pain medications, anti-anxiety medications, sleep aids or selected anti-emetics with sedating side effects. The system of the present invention prompts patients to self-rescue if ventilation is reduced to a critically low level. Specifically, the present invention provides a system that includes calling a patient's name at a certain decibel level and audibly prompting the patient for breaths to reverse severe hypoventilation. According to the present invention, prompts to self-rescue can be effective for at least 15 minutes to maintain blood oxygen saturation above critical low levels until help can be summoned.

The system for detecting breathing of a patient and for providing an alert when an abnormal breathing condition is detected in a patient, comprises:
At least one respiration sensor. The respiration sensor may include at least one sensor on the head (above an airway obstruction) of the patient on the body of the patient below or directly on a possible airway obstruction, or other means such as Wi-Fi modulation;
At least one sensor to detect motion or sufficient lack thereof which may be associated with central apnea; and
A system for delivery of verbal and/or tactile stimulus to the patient to induce them to breathe.

Additionally, the system may use multiple sensor locations or multiple sensor analysis methods to identify the type of apnea (obstructive or central).

The system also includes a processor with programmed logic and memory whereby the response to different types and levels of stimulus, as measured by system sensors, is used identify the proper level of prompting required to continue to promote patient breathing.

Respiration is detected by the system using one or more sensors. The sensors may include sensors to detect one or more of the following:
Changes in pressure as measured in the patient's nostrils and/or mouth;
Changes in the concentration of exhaled CO2 (capnometry) in the patient's nostrils and/or mouth;
Changes in humidity of air in the patient's nostrils and/or mouth;
Changes in temperature as at the patient's nostrils and/or mouth;
Measurement of chest movement/rotation using either an accelerometer, gyroscope or plethysmography band;
Measurement of abdominal movement/rotation using either an accelerometer, gyroscope or plethysmography band;
Measurement of changes in electrical impedance as measured across the chest;
Changes in intensity of light passing through patient tissue (photoplethysmography);
Respiration measurement via radio frequency/Wi-Fi modulation, or other systems known in the art;
Blood oxygen saturation using pulse oximetry; and/or
Respiration measurement via acoustic sensor (microphone) placed over or near the pharynx.

In one embodiment of the invention, the system uses escalating levels of stimulus to induce respiration of the patient.

In another embodiment of the invention, the system uses comparison in respiration measurements between or among multiple sensors to identify the source of apnea (obstructive or central).

The system for detecting abnormal breathing conditions of a patient and systems and methods for providing an alert and patient stimulus when an abnormal breathing condition is detected in a patient according to the present invention includes systems and methods to minimize false positive alarms and to distinguish between various ventilation problem types. The system of the present invention also includes a display to show patient care personnel the ventilation problem type and level of prompting support required to keep the patient safe so a clinician can adjust therapy promptly and according to the specific needs of the patient.

Accordingly, the present invention identifies and distinguishes among drug-induced ventilation problem types, including central apnea, bradypnea, obstructive apnea, and mixed bradypnea with obstructive apnea. When a ventilation problem type is identified, the system prompts the patient by name to breathe and displays the history of breath prompts required to maintain the patient's ventilation as the clinician may be otherwise unaware of the immediate danger to the patient.

The system of the invention may also adjust the voice urgency if the patient fails to properly respond to initial or subsequent voice commands to breathe.

The system of the invention may also include different voice intonations to better mimic the voice of a man, woman or child. In addition, the system may be able to record and use voice commands of a relative of the patient, such as a mother, father, sibling or guardian of which the patient may be familiar.

The present invention further identifies the source of the ventilation problem using a combination of sensors above and below the point of airway obstruction (near the vocal cords). Sensors positioned above the obstruction may include a capnometer, a nasal pressure sensor and/or a thermistor. Sensors positioned below the obstruction may include an abdomen accelerometer, an inclinometer, a gyroscope, a sensor for measuring impedance, or a respiratory inductance plethysmography band.

The system will identify central apnea by detecting a lack of breathing effort/motion at the abdomen (below the point of obstruction) using an accelerometer, gyroscope, inclinometer, of other device known in the art, combined with no breaths detected above the point of obstruction using a capnometer, nasal pressure sensor, and/or thermistor. The system may further identify and confirm central apnea by using a fingerprint of central apnea in the red or infrared photoplethysmography signals of the pulse oximeter.

The system will identify bradypnea by detecting matching breaths marked both above and below the point of obstruction. Bradypnea may further be identified and confirmed using the fingerprint of bradypnea in the red or infrared photoplethysmography signals of the pulse oximeter.

The system will identify obstructive apnea by detecting no breaths above the point of obstruction with a capnometer, nasal pressure sensor, and/or thermistor, while breath attempts continue to be observed below the point of obstruction with an accelerometer, gyroscope, inclinometer, or other device known in the art. Obstructive apnea may further be identified and confirmed using the fingerprint of airway obstruction in the red or infrared photoplethysmography signals of the pulse oximeter.

The system may also incorporate data fusion to include information about respiratory rate that can be simultaneously measured by multiple methods. For example, the pulse oximeter photo plethysmography sensor can provide a backup measure of respiratory rate. Data from the pulse oximeter, respiratory rate or plethysmogram can then be fused with the information above and below the point of obstruction to confirm continued breath attempts.

The system may confirm a life-threatening condition (and a true need for breath prompting) by using a combination of: 1) low blood-oxygen saturation reading from a pulse oximeter (e.g., <85%) and 2) sufficient lack of motion by the finger (used for motion artifact rejection) and 3) lack of sufficient motion by the body (a signal of likely unconsciousness). Alternatively or in addition to, the system may further confirm a life-threatening condition (and a true need for breath prompting) by detecting a sufficient lack of abdominal motion (a signal of likely unconsciousness).

The system of the invention may also include a snooze function that will allow the system to be paused by a care provider to temporarily mute or stop breath prompting while the patient is being attended to, for patient trips to the restroom, for physical therapy or other situations where temporary interruption of breath monitoring is necessary.

In addition, the system of the invention may also display historical information about the number and frequency of system prompts to the patient and the patient's historical responses to such prompts. This allows the clinician to review the effectiveness of the system while the clinician has been away from the patient and to determine if adjustments to the system or patient care are warranted.

The system for detecting abnormal breathing conditions of a patient for providing an alert and patient stimulus when an abnormal breathing condition is detected according to the present invention provides breath promoting in patients experiencing various forms of apnea to cause such patients to self-rescue for a period of time until a care provider can assist the patient. The system of the present invention is configured to repeatedly prompt patients experiencing a form of apnea to breathe in response to audible and/or tactile cues from the system to breathe. If the patient breathes in response to prompting from the system of the present invention three times in a row, the patient is deemed highly responsive to such prompts and are more likely continue to breathe for a period of time, at least up to 15 minutes, until a caregiver can attend to the patient. If however, two of the first three prompts provided by the system instructing the patient to breathe are not successful, the system escalates the prompting level to the next higher level. If the highest level of prompting is not successful, the system immediately initiates an alarm condition alerting the care provider that the patient may be experiencing a life-threatening condition.

The system of the present invention includes or is connected (either directly or remotely) to a display monitor to display current and historical sensor readings and prompting status of the patient. For example, historical information about when the breath prompts were each given and which level of prompting stimulus is being administered can be displayed, as the clinician may be unaware of a potentially dangerous situation when the breath rate and $SpO_2$ appear to be within safe limits.

The display monitor also shows the type of breathing problem identified by the system. A caregiver can better address the root of the problem if the cause of the problem is known. For example, if a central obstruction is the main problem, alternate solutions may include reduction of sedatives or addition of continuous positive airway pressure (CPAP). If central apnea and bradypnea are the dominant problems, a reduction in opioid dosing may be considered.

According to the present invention, the system for detecting abnormal breathing conditions of a patient and for providing an alert and patient stimulus when an abnormal breathing condition is detected in a patient uses the patient's name to prompt for breaths. That is, the system of the present invention includes a list of pre-recorded names that may be selected from an alphabetical list. Once selected the patient's name is used as part of the breath prompting audio track of the system. In addition, the system allows a caregiver to add names to the system database that automatically updates the database of pre-recorded names on all systems according to the present invention.

If a particular patient's name is not included in the existing list, it may be entered into the system by typing with the audible recording of the name recorded by the caregiver. When a new name is entered into the system, the name and associated audio recording of the name is uploaded to a cloud-based storage system and added to the master list for all devices. When a new name is entered, it is also contemplated that the recording may include more than just the patient's name. For example, the recording may include the entire prompt to breathe including the patient's name. Thus, the system may provide a script for the caregiver to read when entering the audio recording for a patient.

Accordingly, the present invention provides a system for detecting abnormal breathing conditions of a patient for providing an alert and patient stimulus when an abnormal breathing condition is detected that includes above and below the point of obstruction of a patient. The system further provides a more reliable method for detecting and monitoring patient breaths by generally ignoring all monitored parameters unless the system detects a lack of sufficient motion combined with a sufficient lack of breathing and/or insufficient SpO2. This is uniquely different from the prior art systems that continuously monitor patients in a clinical setting even when the patient moves, gets cold or otherwise presents a condition that could generate a false alarm.

BRIEF DESCRIPTION OF THE DRAWINGS

The following detailed description of the illustrated embodiments is better understood when read in conjunction with the appended drawings. For the purpose of illustrating the invention, there is shown in the drawings exemplary embodiments which illustrate what is currently considered to be the best mode for carrying out the invention, it being understood, however, that the invention is not limited to the specific methods and instruments disclosed. In the drawings.

DETAILED DESCRIPTION OF THE ILLUSTRATED EMBODIMENTS

Figure 1:
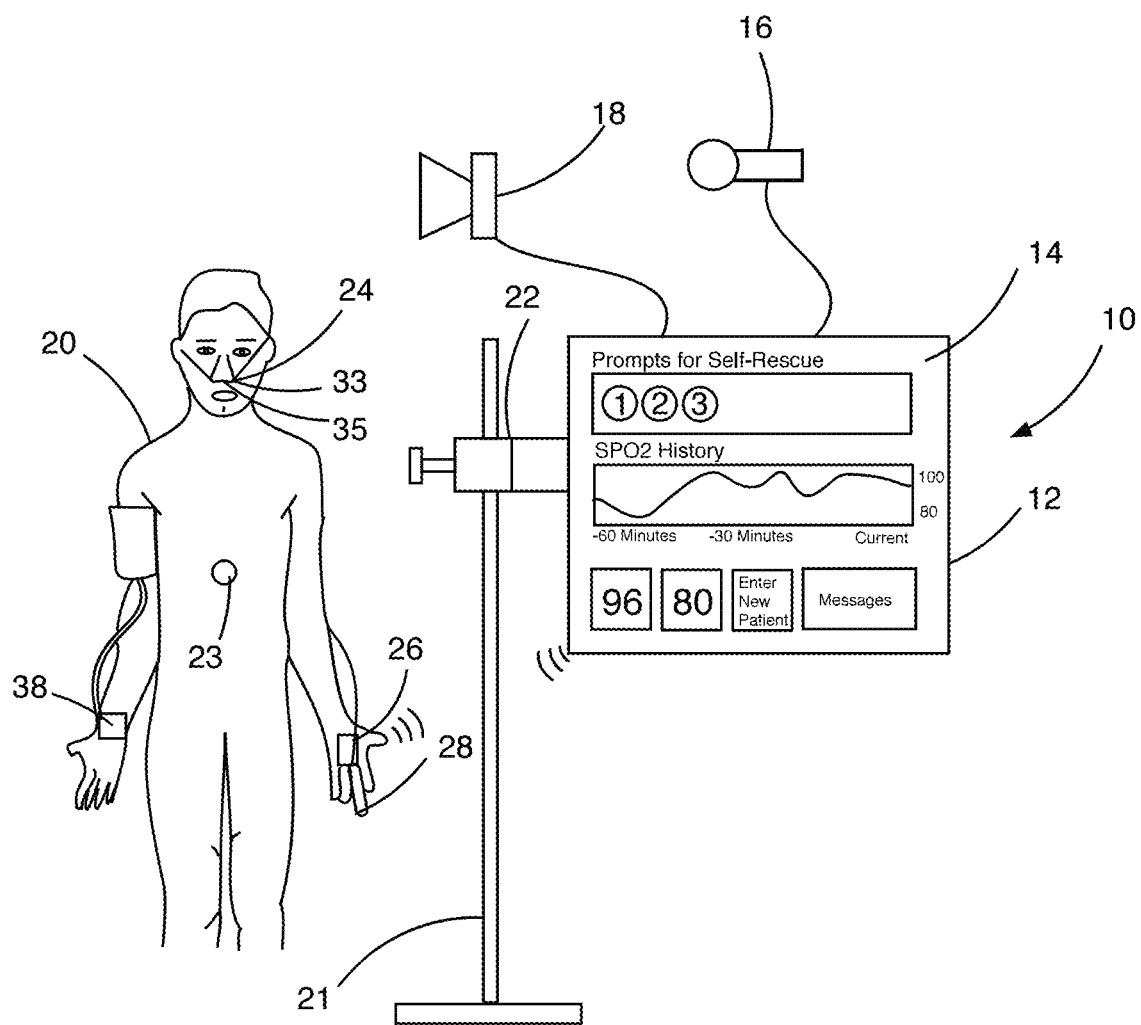
FIG. 1 is a patient-monitoring system for determining, displaying and alerting a patient experiencing ventilation depression in accordance with the principles of the present invention.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. Thus, the full scope of the invention is not limited to the examples that are described below.

The system and method for detecting abnormal breathing conditions of a patient and for providing an alert and patient stimulus when an abnormal breathing condition is detected is configured to detecting ventilatory depression and to automatically prompt a patient with an auditory and if necessary, a combined auditory and tactile stimulus, to breathe. While drug induced ventilatory depression is a well-known cause of adverse events in hospitals and at home, patients consuming opioids and sedatives, especially in combination, need to have their respiratory function continuously monitored and have caregivers immediately available to rescue patients from adverse side effects of these medications. In some hospital settings, an adequate level of monitoring is easily accomplished while in other hospital settings and at home, a continuous level of monitoring and caregiver availability is more difficult to consistently achieve. The system and method of the present invention addresses the gap in monitoring capability by providing a wearable portable monitor that prompts patients to breathe when the system detects ventilatory depression.

The system of the present invention combines signals from $SpO_2$ and motion sensors on a body part, such as a finger, arm, leg, chest, and/or torso, etc. with at least one sensor to identify hypoventilation. In addition, a computer generated voice prompt interacts directly with the patient to arouse the patent using verbal prompts calling the patient by name to breathe via a speaker in audible range of the patient. The direct patient interaction of the system causes reversal of hypoventilation well before an onset of life threatening cardiac arrhythmias and hypoxia. The system displays a history of prompting occurrence so the caregiver will know whether sedative/opioid doses need to be adjusted. If a series of prompts to breathe have not been successful and a low $SpO_2$ threshold has been reached, an alarm will sound and the system will contact the staff, such as via text, phone, or in-facility communication systems to request immediate assistance. The device cross-checks and interprets its sensor sources to determine the correct course of action so that the clinician is alerted only when the patient is experiencing ventilatory depression so that the patient can rest as much as possible and false alarms are reduced while the patient continues to breathe on his or her own.

The system interacts directly with the patient to verbally prompt for breaths during dangerous periods of hypoventilation and potential for low oxygen levels. This process initiates the patient's ability to self-rescue and provides much-needed relief from continual false positive alarms and prolongs the time during which the clinician can intervene to restore adequate ventilation. Prior art monitors rely on summoning a busy clinician with an alarm before a patient is rescued. The system employs digitized verbal prompts to breathe using the patient's name (e.g., "John, take a big breath!"). The system determines the patient's breathing status and personalizes the prompting stimulus to the patient's breath responsiveness. When a prompt is successful in arousing the patient, the level of prompting is not escalated. If, however, a prompt is not successful, the level of prompting is escalated. For example, an initial prompt may use a low volume voice. If the initial prompt is unsuccessful, a second prompt using a loud voice is initiated. If the second prompt is unsuccessful, a third prompt using a loud voice with tactile stimulus is initiated. If the third prompt is unsuccessful, a fourth prompt using a loud voice, tactile stimulus and electrical muscle tetany is initiated. In addition, the caregiver may be alerted at this time.

The system actively monitors and protects the patient when caregivers are not physically present. As a backup measure, if the system does not detect any new breaths despite the prompts for the patient to breathe, it will immediately signal the caregiver to request additional help. A display on the monitor indicates the number of times the system has prompted the patient to breathe and the period of time in which such prompts have been given so caregivers can adjust the pain medication or take other measures as necessary to eliminate the ventilatory depression of the patient as necessary. The system does not require any additional work to set up other than recording the patient's name for prompting if the patient's name is not already entered into the system.

The system utilizes a novel approach to patient monitoring. Specifically, the system utilizes a lack of breaths and sufficient lack of motion rather than seeking to continue reporting breaths despite patient motion. A ventilation sensor (respiratory rate, tidal volume or minute volume) and body motion input signals from patient sensors are combined to initiate digitized verbal and tactile breath prompting. Other patient signals may be employed as well. Rather than filtering the ventilation signal in order to "read through patient motion" to extract the most accurate information about ventilation during body and hand motion, the system of the present invention detects insufficient ventilation during periods when the patient is no longer moving. That is, if a patient is not moving and depressed ventilation is detected, the patient is likely either unconscious or the insufficient ventilation signal is most likely not to be caused by a motion artifact.

The system is also able to determine what type of ventilation problem the patient may be experiencing, such as central apnea, obstructive apnea, bradypnea, partial airway obstruction or combinations thereof. Continuous respiratory rate monitoring is configured to detect apnea caused by either lack of central respiratory drive or by airway obstruction resulting from relaxed airway muscles. Comparing respiration monitoring between or among multiple sensors makes it possible to discern central apnea from obstructive apnea. A patient experiencing a ventilation problem can be a result of central apnea, obstructive apnea, bradypnea, partial airway obstruction or a combination of these conditions. If a clinician is made aware of the type of ventilation problem, he or she will be better informed in order to make changes that will keep the patient safe. For example, if the ventilation problem is central apnea and the patient is receiving opioids to treat pain, the clinician may consider reducing the opioid dose. If the ventilation problem is obstructive apnea, application of Continuous Positive Airway Pressure or other ventilation assist methods may be more appropriate.

When administered drugs, body habitus, disease states, airway anatomy, rapid eye movement (REM) sleep, REM rebound sleep, and other factors interact, which can lead to a patient being incapable of maintaining sufficient ventilation and oxygenation. Moreover, it is very difficult to predict which people will experience difficulties with adequate breathing and require assistance and which ones will not.

As shown in FIG. 1, patient-monitoring system, generally indicated at 10 utilizes a computer-based system monitor 12 that includes a touch screen display 14 providing a user interface. The monitor 12 includes a processor and internal memory in order to be able to load and run the computer software patient monitoring program according to the present invention. The monitor 12 may employ a Windows®-based operating system, an Apple®-based operating system, a UNIX®-based operating system or other operating systems known in the art. In addition, the monitor may be in the form of a personal computer or a handheld device such as a tablet or smartphone. The system 10 also includes a microphone 16 for audio recording, a speaker 18 for providing audio prompts to the patient 20. The system also includes a tactile stimulator 38 that may be attached to the wrist of the patient 20 as shown or on the shoulder or other body location of the patient. The tactile stimulator 38 provides additional stimulation to the patient 20 when attempting to cause the patient to self-rescue if audio prompts alone are not successful. For example, the tactile stimulator 38 may comprise a massager attached to the shoulder, arm or other body part of the patient and/or an electro-stimulation device attached to the patient in order to waken and/or arouse the patient 20. In addition, the level of vibration and/or electro-stimulation may be increased in each successive prompt to breathe if the patient is unresponsive. The system may further be provided with an IV pole clamp 22 so that the monitor 12 can be attached to an IV pole 21 near the patient 20.

Figure 2:
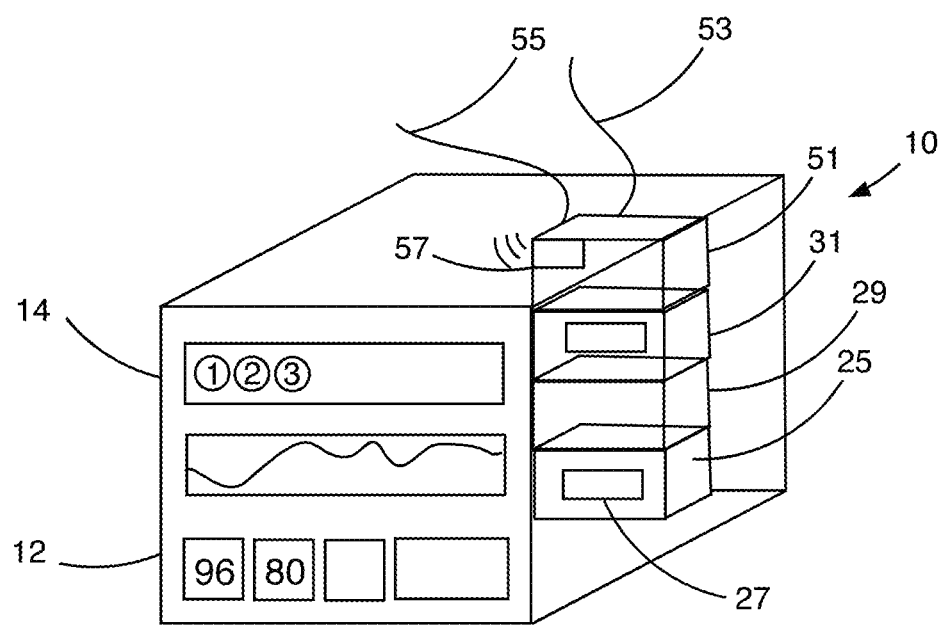
FIG. 2 is a computer-based system for determining, displaying and alerting a caretaker that a patient is experiencing ventilation depression in accordance with the principles of the present invention.

As shown in FIG. 2, a software program 27 of the present invention is provided in memory 25 of the monitor 12 and includes a data processing system run by the processor 29 for interpreting data received by the data receiver 31 from the various patient as 23, 24 and 28 and determining whether the patient 20 is experiencing ventilatory depression. Referring again to FIG. 1, the patient sensors include a capnometry sensor 24 that collects ventilation data at 100 Hz. Alternatively or in addition, the sensors may include a nasal pressure sensor 33 and/or a thermistor 35. The various sensors are communicated to the data input device 51, which may be electrically coupled via wires 53 and 55 to the sensors or wirelessly via wireless communication transceiver 57, such as a Blue Tooth or Wi-Fi communication module. These sensors are used to detecting ventilatory depression of a patient by detecting at least one of inadequate breathing or lack of breathing in the patient by measuring at least one of: pressure, CO2, humidity or temperature at the mouth or nostrils; sound at the larynx; photoplethysmography; radio frequency/Wi-Fi modulation; or chest impedance. In addition, sensors are provided to detect chest movement or rotation.

Figure 3:
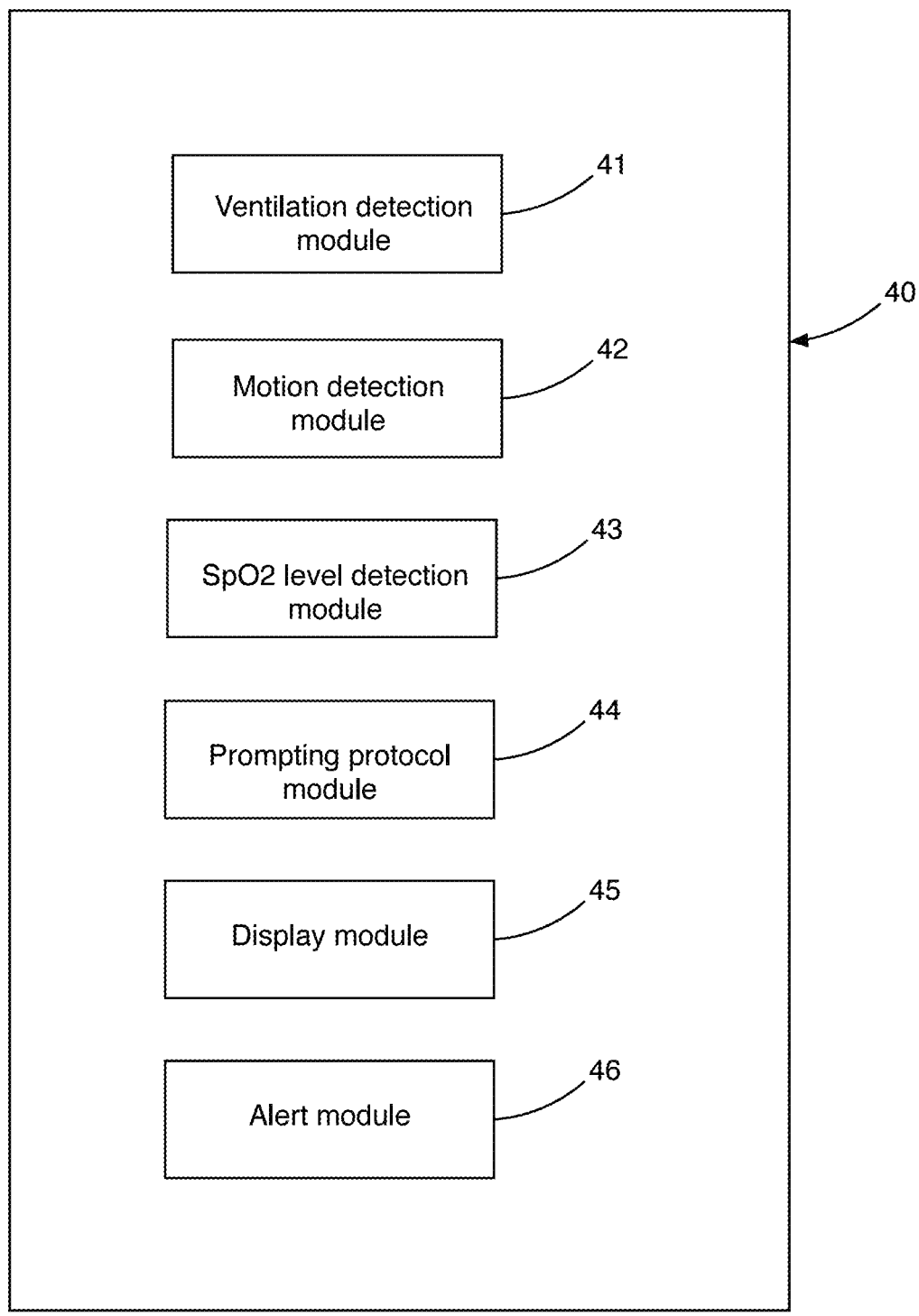
FIG. 3 is a schematic block diagram of a software system of the present invention for detecting ventilation, motion and SpO2, prompting, displaying and alerting in accordance with the principles of the present invention.

As shown in FIG. 3, the computer software system 40 of the present invention includes various subsystems to detect certain patient conditions, to determine whether patient prompting to breathe meets a threshold of adequate patient ventilation to ensure patient safety. The computer software system 40 is comprised of various hardware systems to gather patient data and provide the data to the processor of the system, to alert the patient to breathe and to provide display and care giver alerts. Each of these hardware components are in communication with the computer system software 40. The computer system software 40 includes a number of subroutine or modules. The ventilation detection module 41 receives data from the patient's ventilation detection system that indicates whether the patient is breathing. The patient's ventilation detection system may include various sensors that are capable of determining if the patient is breathing, such as respiratory rate. The motion detection module 42 receives data from the patient's motion detection system, that include one or more sensors configured to detect if the patient is moving and, if so, if such movement is sufficient to indicate that the patient is alert. The SpO2 level detection module receives data from a SpO2 sensor coupled to the patient to determine the patient's SpO2 level to indicate if the patient is sufficiently oxygenated. If one or more of the ventilation detection module 41, motion detection module or SpO2 level detection module determine that the patient is not being properly ventilated, the prompting protocol module 44 is triggered. As is described in more detail herein, the prompting protocol module 44 is connected to a speaker to provide audible breathe prompting to the patient and one or more tactile patient stimulation devices to provide tactile stimulation to the patient if audible breath prompting is not sufficient. For example, the prompting protocol module will prompt the patient when $SpO_2$ drops at least 4 percentage points from baseline or below 85% for more than 10 seconds or respiratory rate is less than 6-10 breaths/min. The system 10 stops prompting the patient when $SpO_2$ increases more than 4 percentage points from the nadir or above 90% for more than 10 seconds and respiratory rate is greater than 6-10 breaths/min. The system 40 is configured to activate the alert module 46 when breath prompting is long lasting or ineffective as determined by the system 40. The $SpO_2$ level detection module includes a filter that is based on an assumption that if an accelerometer connected to the motion detection module and coupled to the patient detects sufficient hand and/or body motion, the patient is still conscious and a low $SpO_2$ measured value that has been measured can be ignored. The alert module 46 is coupled to one or more caregiver alert systems, such as an audible alarm, a wired or wireless communication device to transmit a warning signal to a caregiver, such as to a work station, mobile alert system or the like. In addition, a display module of the system 40 is in communication with a display monitor to display historical and real-time information of the system. For example, the display module 45 will display the patient's historical and real-time ventilation status and/or conditions, the patient's historical and real-time level of movement, the patient's historical and real-time SpO2 levels and the patient's historical and real-time prompting protocol cycles and status. By providing this information on the display, a care giver can review the patient's breathing history and can see whether the patient has been self ventilating or has required breathing assistance by prompting from the system 40.

Referring again to FIG. 1, the system 10 further includes a finger pulse oximeter 28 (such as that manufactured by MasimoSET, Masimo, Irvine, Calif.). The system 10 further includes a digital three-axis accelerometer 26 (such as a ADXL345 manufactured by Analog Devices, Norwood, Mass.) with a range of ±16 g (±156.96 m s$^{-2}$; set to a sensitivity of ±2 g). The capnometry sensor 24 may be a LoFlo, manufactured by Philips Medical, Wallingford, Conn.). The sensors may include a battery powered microcontroller (Arduino Mega 2560 (R3) manufactured by Arduino, Ivrea, Italy), and Bluetooth LE transceiver (Bluefruit LE nRF8001, manufactured by Adafruit, NYC, N.Y.). The accelerometer signal is sampled at 100 Hz at a sensitivity of ±2 g (±19.62 m s$^{-2}$) with a resolution of 10 Bits (4 mg/LSB scale range). Using a mixed programming approach available in LabVIEW 2015 (National Instruments Inc., Austin, Tex.) and MATLAB 2008b (MathWorks Inc., Natick, Mass.), the accelerometer signals are bandpass filtered by a 5th order Butterworth filter with a lower cutoff frequency of 150 and an upper cutoff frequency of 800 Hz to reduce the amplitude of cardiogenic oscillations, common electronic noise at 60 Hz and high-frequency noise.

While various sensors have been described herein, it is also contemplated that a single sensor on the abdomen of the patient may be used. That is, the system may employ a single accelerometer/gyroscope sensor to differentiate airway obstruction from hypoventilation. Of course, the addition of other sensors as herein described adds to the ability to quickly and accurately diagnose the type of breathing obstruction being experienced by the patient.

To prove effectiveness of the system 10 of the present invention, a study was conducted with volunteers receiving the sedative propofol and the opioid remifentanil to produce respiratory depression and airway obstruction. Volunteers were alternately prompted to breathe utilizing voice commands provided by the system 10. Alternatively volunteers were verbally prompted by a nurse. Each group was assigned to follow one of two trajectories: i) higher likelihood of respiratory depression and apnea (higher opioid, lower sedative) and ii) a higher likelihood of airway obstruction (higher sedative, lower opioid, per the drug interaction models 30 of FIG. 1. Remifentanil and propofol were administered to target predicted effect site concentrations using a Stanpump and a computer assisted infusion pump. Pharmacokinetic parameters published by Minto et al. and Schnider et al. were used for remifentanil and propofol respectively.

A pulse oximeter 28 and a 3-axis accelerometer 26 were placed on the left index finger and a capnometer 24 monitored respiration. Drug concentrations were increased stepwise in 15 steps. After each of the 15 steps in drug effect-site concentration, the accelerometer signals and corresponding pulse oximeter signals were recorded continuously before and during prompting for breaths. During periods of hypoventilation, some volunteer patients were prompted by the system 10 to breathe. Other volunteer patients during period of hypoventilation were verbally prompted by a nurse to breathe. Verbal commands were spoken at 85 dB or 100 dB. The system 10 prompted for breaths by the patient first using a low voice, then a loud voice and finally with a loud voice together with muscle tetany. The effectiveness of prompting by the system 10 was compared to the effectiveness of prompting by a nurse at each level of drug administered.

Figure 4:
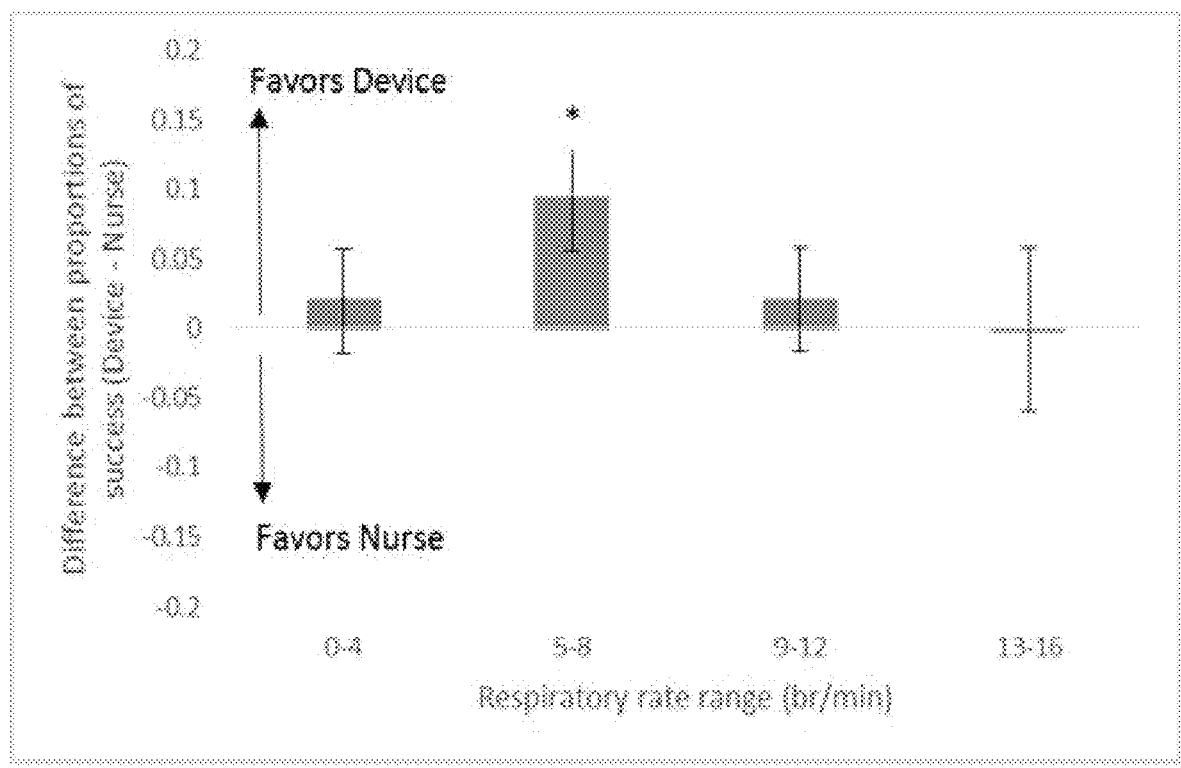
FIG. 4 is a graph showing a difference between proportions of success comparing the patient-monitoring system in accordance with the principles of the present invention verses an actual nurse when prompting a patient to breathe at various respiratory rate ranges.

FIG. 4 is a graph illustrating the difference between proportions of success comparing the system 10 verses an actual nurse when prompting a patient to breath at various respiratory rate ranges in breaths per minute. As shown in FIG. 4, the digitized voice prompts of the system 10 performed as well as or better than the nurse for initiating breaths and patient rescue regardless of the baseline respiratory effort. In fact, there was no difference between the system 10 and nurse except at a respiratory rate of 5-8 br/m in, which favored the system 10. These tests show that even when a patient experiences extreme hypoventilation and apnea, the system 10 is as effective as a live nurse in prompting a patient to breathe.

Figure 5:
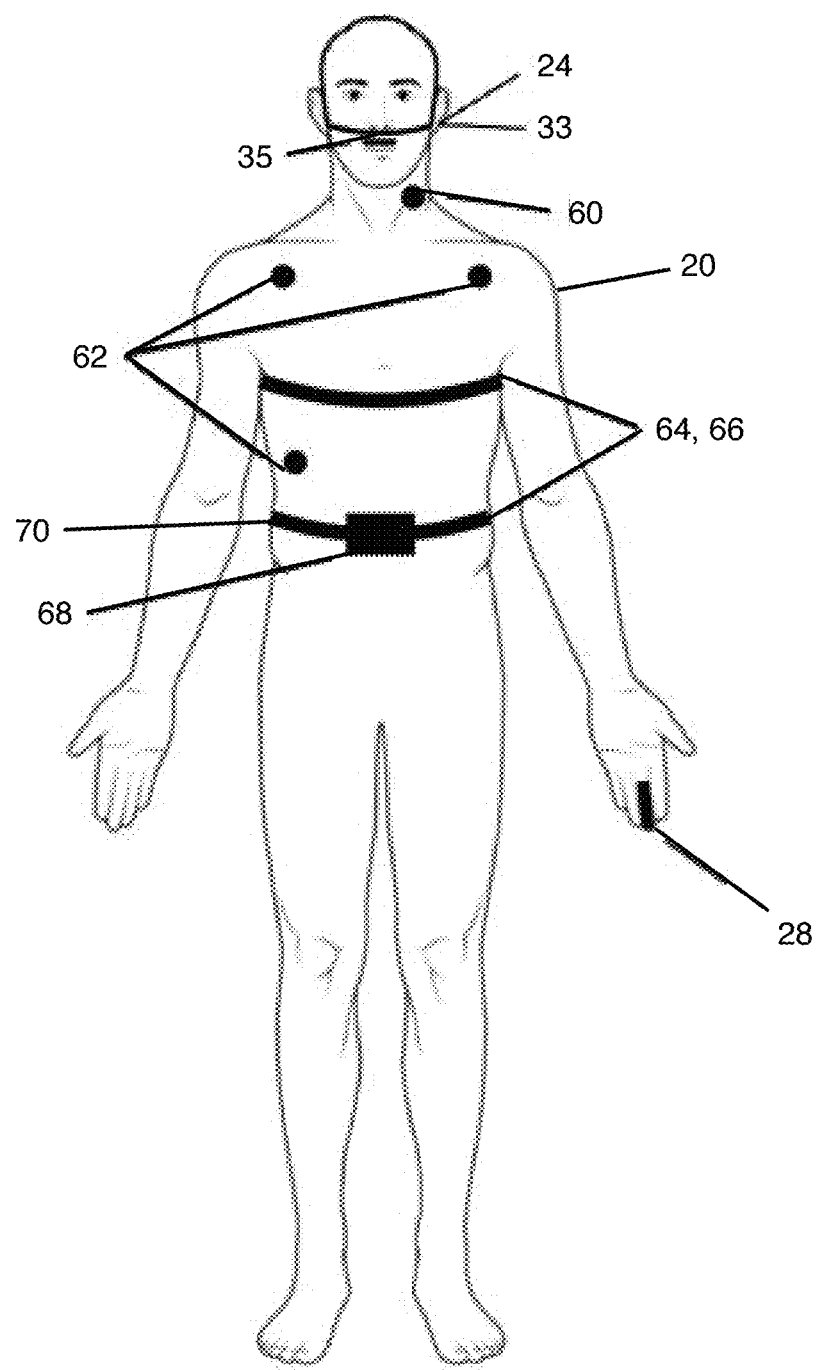
FIG. 5 is a front view of a patient to which various sensors of the patient-monitoring system used to detect patient breathing and movement are attached to the patient so that the system can determine whether the patient may be experiencing ventilatory depression.

FIG. 5 illustrates the various sensors of the system 10 used to detect patient breathing and movement so that the system 10 can determine whether the patient may be experiencing ventilatory depression. To detect whether the patient is breathing, a nasal capnometry sensor 24, pressure sensor 33, such as a pressure transducer, and oronasal thermistor 35 are attached to the head of the patient 20. These sensors detect whether air is entering or exiting the nasal passages of the patient 20. Attached to the neck of the patient is a peri-tracheal microphone 62 to detect whether the patient is breathing by detecting the sound of air flowing through the trachea of the patient. Attached to the torso of the patient 20 are a plurality of transpulmonary electrical impedance leads 62 that can be utilized for electrical impedance tomography (EIT). EIT is a method for displaying lung movement of a patient to detect breathing and ventilation. Sensors 64 and 66 for respiratory inductance plethysmography for the chest and abdomen are employed for evaluating pulmonary ventilation by measuring the movement of the chest and abdominal walls. These sensors 64 and 66 are comprised of belts that wrap around the torso of the patient 20. An accelerometer 68 is attached to a belt 70 that is attached at the waist of the patient 20. The accelerometer 68 can detect abdomen and/or chest movement or rotation. A photolethysmography sensor 28 is attached to the finger of the patent to measure the patient's pulse. Each of these sensors are coupled to the system, either by wires or wirelessly, and provide data to the system in evaluating the patient's ventilation as well as whether the patient positively responds to breathing prompts provided by the system.

Figure 6:
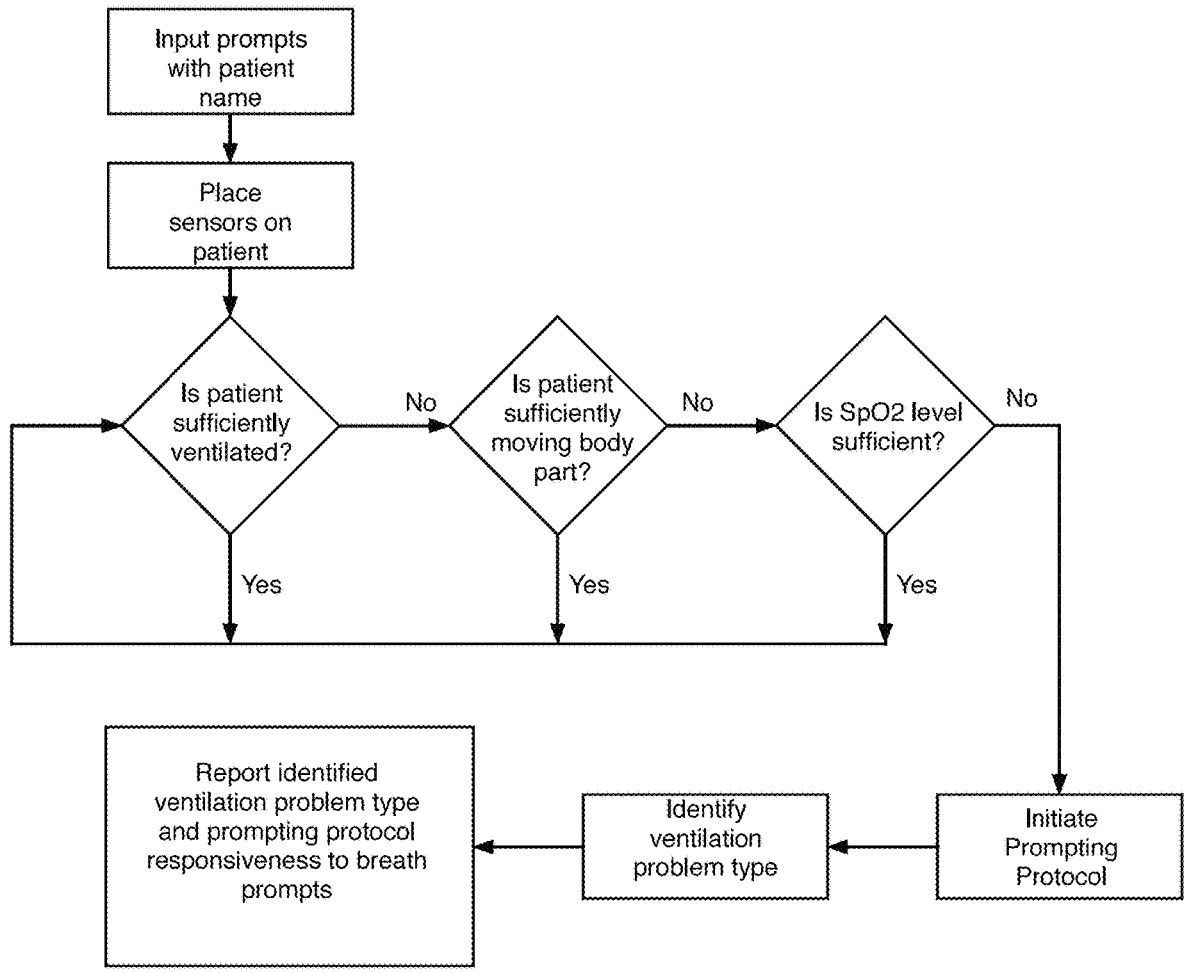
FIG. 6 is a schematic flow diagram of a method of detecting insufficient ventilation and prompting a patient to breathe in accordance with the principles of the present invention.

As shown in FIG. 6, a method of detecting insufficient ventilation and prompting a patient to breath is illustrated. Initially, the patient's name is audibly recorded into the system and become part of the system database with other recorded names. One or more sensors are placed on the patient to detect whether the patient may be experiencing a lack of sufficient ventilation. If so, the system also detects whether the patient is moving, whether by hand, finger or other body part. If no motion is detected, the system determines that the patient is experiencing depressed ventilation and checks the SpO2 level to determine if it is sufficient. If the SpO2 level is low, this indicates that the patient is experiencing an oxygenation problem. Based on the sensor used to detect whether the patient is breathing and other sensor data, the system will initiate the prompting protocol to prompt the patient to breath. In addition, the system will utilize the sensor data to identify the type of ventilation problem the patient is most likely experiencing. As will be described in more detail, when the prompting protocol is initiated, the patient is prompted to breathe in an escalating manner based on patient responsiveness to audible and/or tactile cues provided by the system to breathe. Information about the system's effectiveness in prompting the patient to breathe is reported to and displayed on the patient monitoring system.

Figure 7A:
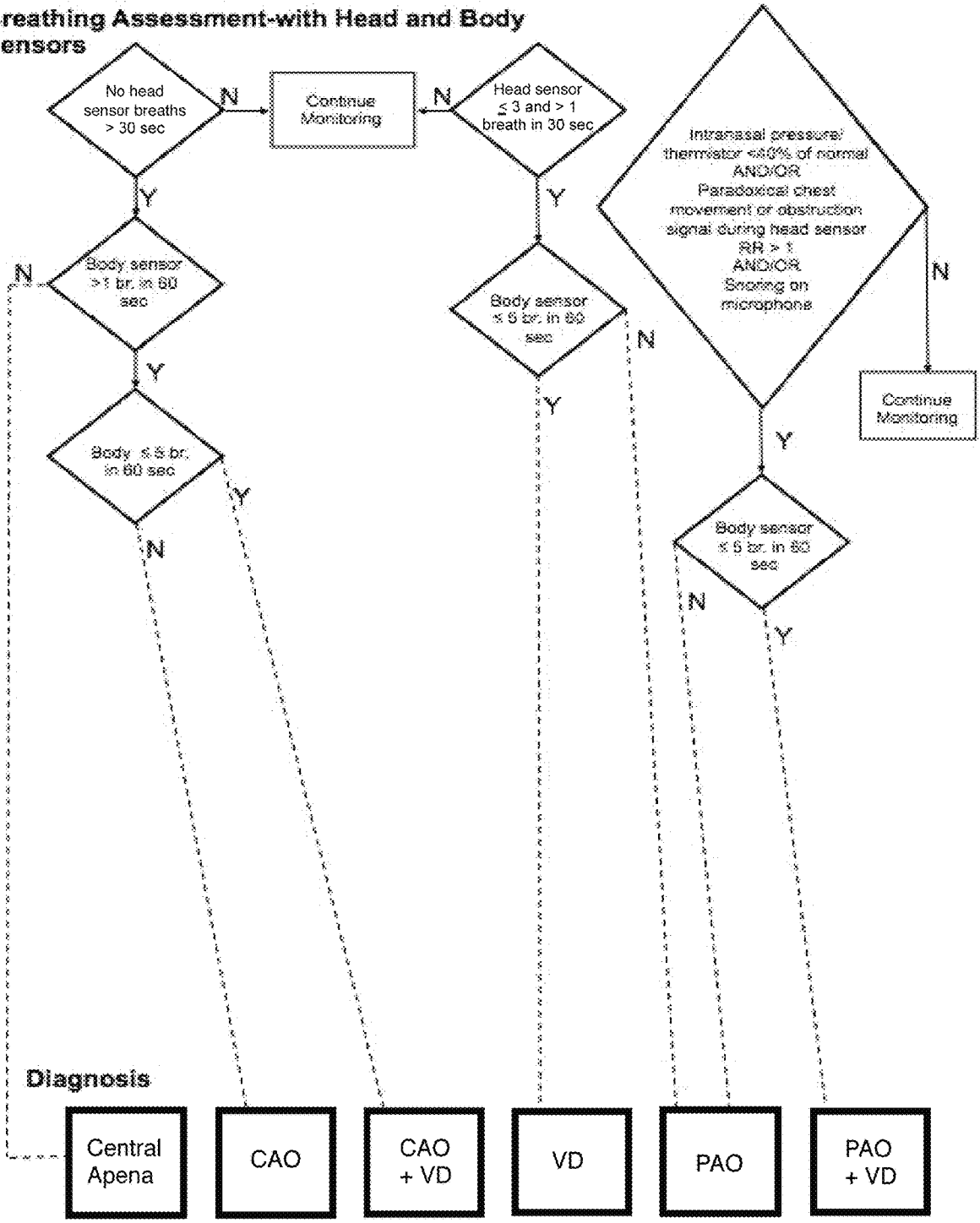
FIG. 7A is a schematic flow diagram of a first embodiment of a method of diagnosing respiration events in real time based on various real time sensor readings of the patient-monitoring system of the present invention.

As shown in FIG. 7A, the system is able to classify respiration events in real time based on the various real time sensor readings of the system of the present invention. In FIG. 7A, the system includes both head and body sensors. If the head sensor(s) does not detect any breaths in the last 30 seconds, the system will then determine if the body sensor has detected at least 1 breath in the last 60 seconds. If not, the patient is most likely experiencing central apnea. Thus, central apnea is defined as no breaths in at least 30 seconds. If the head sensor signals (above the point of obstruction) are not available, the system may discern among central apnea, ventilatory depression (VD) (i.e., slow breath rate, bradypnea), and VD combined with various types of possible airway obstruction.

If the body sensor detects at least 1 breath in the last 60 seconds but has not detected at least 6 breaths in the last 60 seconds, the patent is attempting to breathe more slowly and thus likely experiencing complete airway obstruction (CAO) and VD. Thus, ventilatory depression is defined as hypopnea, with a slow breath rate of lower than 3 and greater than 2 breaths per 30 seconds.

If the body sensor has not detected at least 1 breath in the last 60 seconds but detects at least 6 breaths in the last 60 seconds, the patent is attempting to breathe comparatively more rapidly and thus likely experiencing complete airway obstruction (CAO).

Simultaneously, the system of FIG. 7A is also determining whether the head sensor has detected at least 3 breaths with less than 1 breath in the last 30 seconds. If so, and if the body sensor detects less than 6 breaths in the last 60 seconds, the patient is likely experiencing ventilation depression (VD). If, however, the body sensor detects at least 6 breaths in the last 60 seconds the patient is likely experiencing a partial airway obstruction (PAO).

In order to confirm a partial airway obstruction (PAO) or a partial airway obstruction (PAO) combined with ventilation depression (VD), data from an intranasal pressure/thermistor and/or paradoxical chest movement data and/or obstruction signal and/or sound from a microphone is utilized. For the intranasal pressure/thermistor <40% of normal, "normal" may be determined by an average of the highest pressure readings observed during the first 5 minutes of the monitoring session and intermittently during the monitoring session. The intermittent measurements may be based on an average of the 3-10 highest pressure readings observed before an event or on an average value for 3-10 breaths at selected intervals. In addition, paradoxical chest movement may be determined by chest bands summing to nearly zero or waveforms out of phase with respect to each other. Snoring may be detected by the microphone that detects sound identified as snoring. If the intranasal pressure/thermistor data shows a 40% reduction from normal and/or the paradoxical chest movement or obstruction signal when the head sensors is detected less than 6 breaths and more than 1 breath in the past 60 seconds and/or if the sound from the microphone indicates that the patient is snoring, then the system checks the body sensor data to determine if the patient has breathed less than 5 times in the past 60 seconds. An obstruction may be determined by a rotation event detected by a gyroscope or accelerometer detecting rotation indicative of airway obstruction.

If not, the patient likely has a partial airway obstruction (PAO). If so, however, the patient likely has a partial airway obstruction (PAO) and ventilation depression (VD). Results of the breathing assessment are displayed by the system on the system monitor so that a caregiver is notified of the type of breathing problem that the patient may be experiencing so that corresponding corrective action can be taken based on the actual condition of the patient at that time.

Figure 7B:
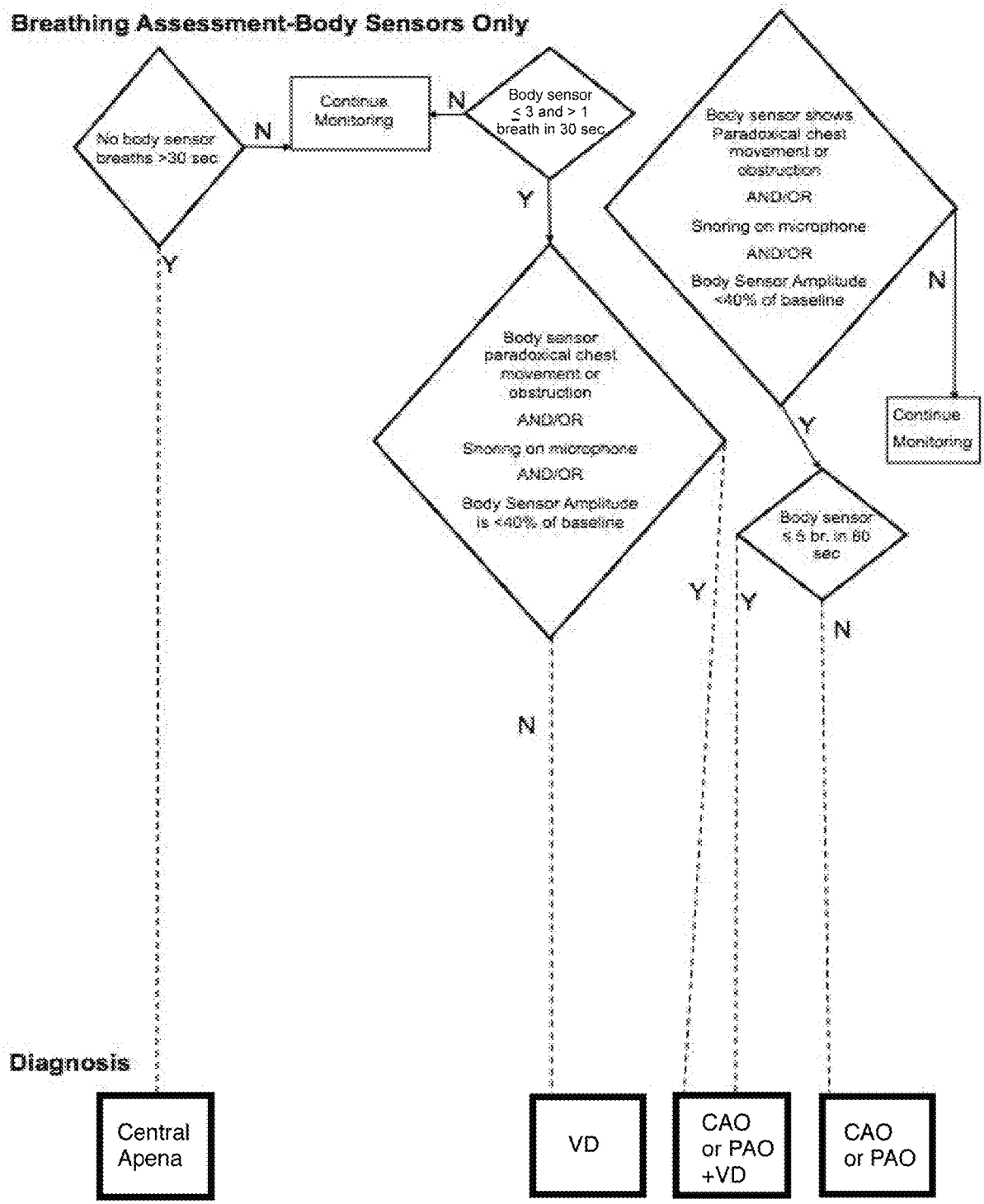
FIG. 7B is a schematic flow diagram of a second embodiment of a method of diagnosing respiration events in real time based on various real time sensor readings of the patient-monitoring system of the present invention.

As shown in FIG. 7B, the system is able to classify respiration events in real time based on the various real time body sensor readings of the system of the present invention. If the body sensor(s) does not detect any breaths in the last 30 seconds, the patient is most likely experiencing central apnea. Simultaneously, the system of FIG. 7B is also determining whether the body sensor has detected at least 3 breaths with less than 1 breath in the last 30 seconds. If so, and if data from a body sensor indicates paradoxical chest movement data and/or obstruction and/or if sound from a microphone indicates snoring and/or if the body sensor amplitude is less than 40% of a baseline, the patient is likely experiencing complete airway obstruction (CAO) or partial airway obstruction plus ventilation depression (PAO+VD). If not, the patient is likely experiencing ventilation depression (VD). Furthermore, in order to determine if the patient is experiencing complete or partial airway obstruction with or without ventilation depression, if data from the body sensor indicates paradoxical chest movement data and/or obstruction and/or if sound from a microphone indicates snoring and/or if the body sensor amplitude is less than 40% of a baseline and the body sensor detects less than 6 breaths in 60 seconds, the patient is likely experiencing complete airway obstruction (CAO) or partial airway obstruction plus ventilation depression (PAO+VD). If the body sensor detects more than 5 breaths in the last 60 seconds, the patient is likely experiencing complete airway obstruction (CAO) or partial airway obstruction (PAO) without ventilation depression. Again, results of the breathing assessment are displayed by the system on the system monitor so that a caregiver is notified of the type of breathing problem that the patient may be experiencing so that corresponding corrective action can be taken based on the actual condition of the patient at that time.

Figure 8A:
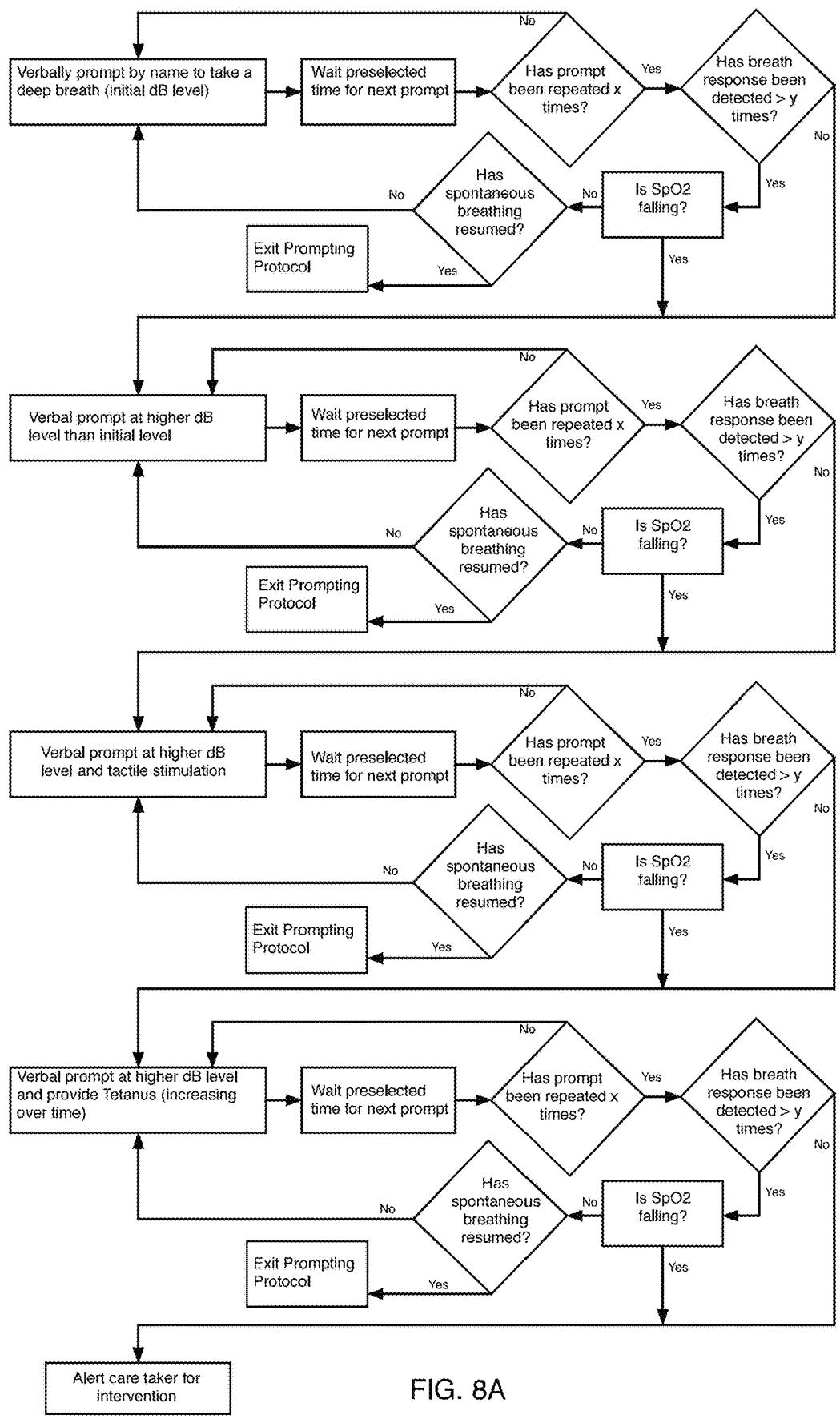
FIG. 8A is a schematic flow diagram of a prompting protocol of the patient-monitoring system of the present invention to prompt a patient to breathe.

Referring now to FIG. 8A, the system of the present invention further comprises a prompting protocol to prompt the patient to breathe. The prompting protocol is linked to the patient monitoring system so that the system can determine in real time whether the prompting is required and if the prompting protocol is having a positive effect on the patient's breathing pattern or whether caregiver intervention is immediately required. Moreover, the prompting protocol of the present invention provides continuous patient monitoring and prompting to breathe when the system detects that the patient is not being properly ventilated until a health care provider can intervene if necessary. Once the system determines that the patient is experiencing ventilatory depression as described above, the system initiates the prompting protocol. When the first level of the prompting protocol is initiated, the patient is prompted with a verbal prompt to take a deep breath by patient name at an initial decibel level, e.g., 65 dB. The first level is repeated up to a set number of times (x), which may vary from between 1 to about 5, in time intervals of between 1 and about 25 seconds depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the first level) and if SpO2 levels are falling below a predetermined level (e.g., adequate levels for patient safety, such as 85%), the second level of the prompting protocol is initiated. If, however, SpO2 levels are sufficient but the patient has not resumed spontaneous breathing, the system will continue prompting at the first level. If SpO2 levels are adequate and the patient has resumed spontaneous breathing as detected by the patient sensors of the invention, the prompting protocol is exited until the system determines that the patient has reverted back to a condition of inadequate ventilation.

When the second level of the prompting protocol is initiated, the patient is again prompted to breathe with a verbal command using the patient's name at a relatively higher decibel level, e.g., 80 dB. The second level is repeated up to a set number of times (x), which may vary from between 1 to about 5, in time intervals of between 1 and about 25 seconds (which may be a shortened period from the first level) depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the second level) and if SpO2 levels are falling below a predetermined level (e.g., adequate levels for patient safety, such as 85%), the third level of the prompting protocol is initiated. If, however, SpO2 levels are sufficient but the patient has not resumed spontaneous breathing, the system will continue prompting at the second level. If SpO2 levels are adequate and the patient has resumed spontaneous breathing as detected by the patient sensors of the invention, the prompting protocol is exited until the system determines that the patient has reverted back to a condition of inadequate ventilation.

When the third level of the prompting protocol is initiated, the patient is again prompted to breathe with a verbal command using the patient's name at a relatively higher decibel level, e.g., 80 dB and the patient is physically stimulated by a tactile stimulator, e.g., low level vibration at the shoulder of the patient. The third level is repeated up to a set number of times (x), which may vary from between 1 to about 5, in time intervals of between 1 and about 25 seconds (which may be a shortened period from the second level) depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the second level) and if SpO2 levels are falling below a predetermined level (e.g., adequate levels for patient safety, such as 85%), the fourth level of the prompting protocol is initiated. If, however, SpO2 levels are sufficient but the patient has not resumed spontaneous breathing, the system will continue prompting at the third level. If SpO2 levels are adequate and the patient has resumed spontaneous breathing as detected by the patient sensors of the invention, the prompting protocol is exited until the system determines that the patient has reverted back to a condition of inadequate ventilation.

When the fourth level of the prompting protocol is initiated, the patient is again prompted to breathe with a verbal command using the patient's name at the higher decibel level that may be 20 dB or more higher than the lower decibel level (e.g., 80 or 100 dB+/−20 dB and the patient is electrically stimulated. The electrical stimulation may start at approximately 10 mA and increase over time, such as in 10 mA increments every 10 seconds up to about 50 mA. The electrical stimulation is halted at the level at which the patient responds. The fourth level is repeated up to a set number of times (x), which may be only once, in a time interval of between 1 and about 25 seconds (which may be a shortened period from the third level) depending on the condition of the patient, the type of sedation that the patient may be under and/or other factors. If the patient does not respond, the patient requires immediate intervention from a healthcare provider, which may be an anesthesiologist, nurse, other clinician, or other caretaker to use both verbal and tactile stimuli. If at any time, the SpO2 of the patient drops below 85% for 10 seconds during the prompting protocol, the prompting level may be immediately escalated. If the highest level of prompting is being used and the SpO2 of the patient drops below 85% for 10 seconds, the system will alert the caretaker that the patient is in danger. If the patient has not resumed spontaneous breathing, the system will continue prompting at the fourth level. If SpO2 levels are adequate and the patient has resumed spontaneous breathing as detected by the patient sensors of the invention, the prompting protocol is exited until the system determines that the patient has reverted back to a condition of inadequate ventilation.

Figure 8B:
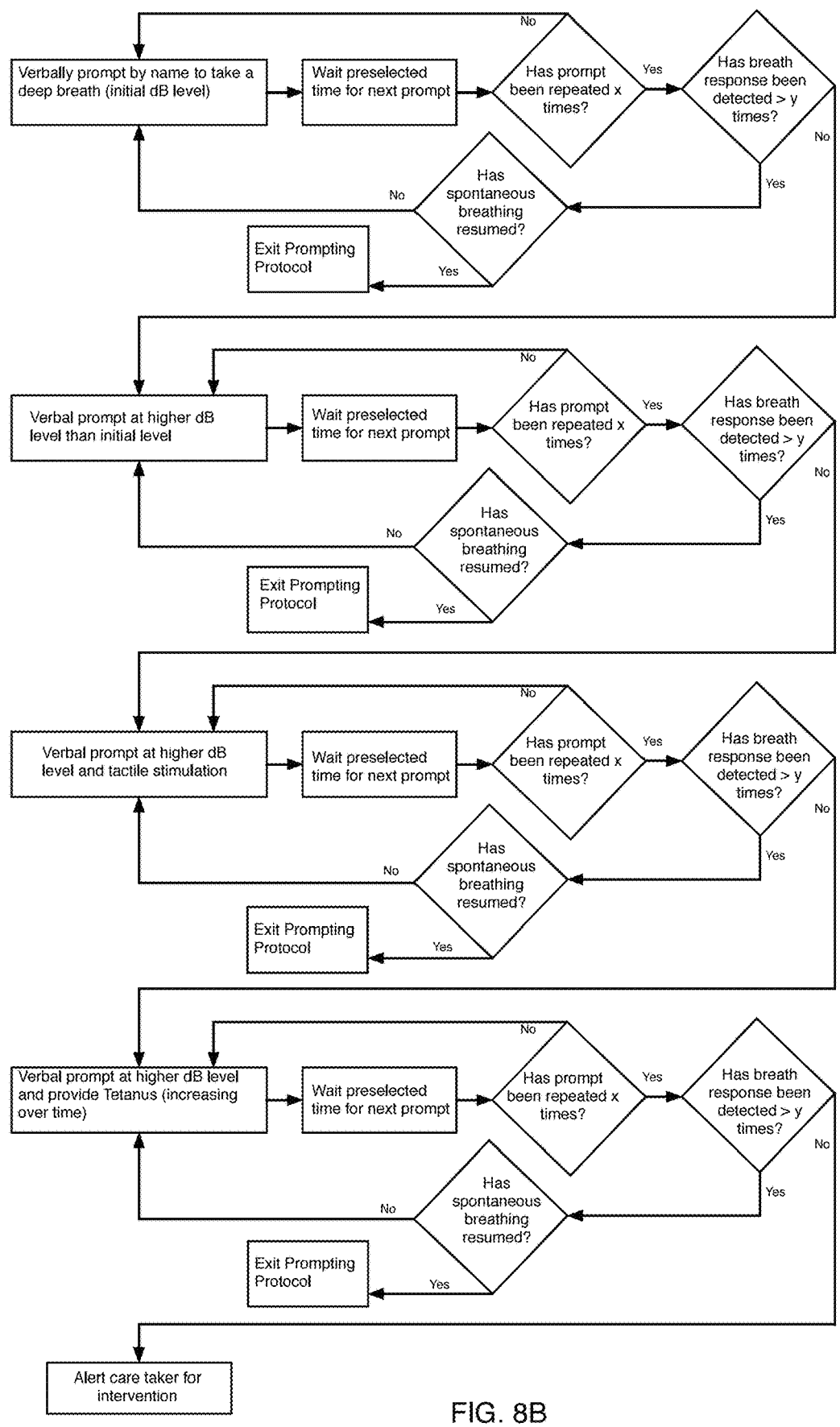
FIG. 8B is a schematic flow diagram of an alternative prompting protocol of the patient-monitoring system of the present invention to prompt a patient to breathe.
Figure 9:
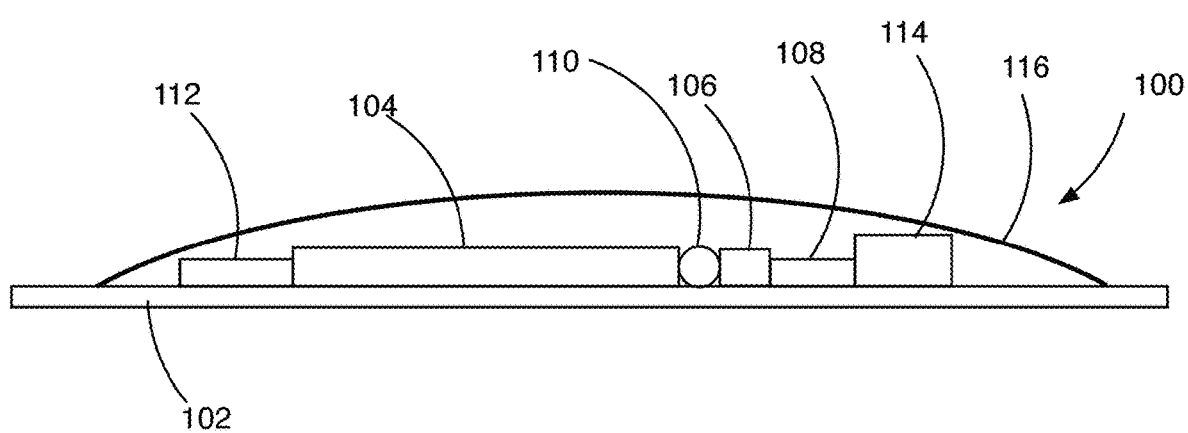
FIG. 9 is a side view of a patient sensor harness in accordance with the principles of the present invention.

As further shown in FIG. 8B, a prompting protocol may be employed according to the present invention when the SpO2 of the patient is not known and/or is not being measured. The prompting protocol of FIG. 8B is linked to the patient monitoring system so that the system can determine in real time whether the prompting is required and if the prompting protocol is having a positive effect on the patient's breathing pattern or whether caregiver intervention is immediately required. Moreover, the prompting protocol of the present invention provides continuous patient monitoring and prompting to breathe when the system detects that the patient is not being properly ventilated until a health care provider can intervene if necessary. Once the system determines that the patient is experiencing ventilatory depression as described above, the system initiates the prompting protocol. When the first level of the prompting protocol is initiated, the patient is prompted with a verbal prompt to take a deep breath by patient name at an initial decibel level, e.g., 65 dB+/−20 dB. The first level is repeated up to a set number of times (x), which may vary from between 1 to about 5, in time intervals of between 1 and about 25 seconds depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the first level) and if SpO2 levels are falling below a predetermined level (e.g., adequate levels for patient safety, such as 85%), the second level of the prompting protocol is initiated. If the patient has not resumed spontaneous breathing, the system will continue prompting at the first level. If the patient has resumed spontaneous breathing as detected by the patient sensors of the invention, the prompting protocol is exited until the system determines that the patient has reverted back to a condition of inadequate ventilation.

When the second level of the prompting protocol is initiated, the patient is again prompted to breathe with a verbal command using the patient's name at a relatively higher decibel level, e.g., 80-100 dB. The second level is repeated up to a set number of times (x), which may vary from between 1 to about 5, in time intervals of between 1 and about 25 seconds (which may be a shortened period from the first level) depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the second level), the third level of the prompting protocol is initiated. If the patient has not resumed spontaneous breathing, the system will continue prompting at the second level. If the patient has resumed spontaneous breathing as detected by the patient sensors of the invention, the prompting protocol is exited until the system determines that the patient has reverted back to a condition of inadequate ventilation.

When the third level of the prompting protocol is initiated, the patient is again prompted to breathe with a verbal command using the patient's name at a relatively higher decibel level, e.g., 80-100 dB and the patient is physically stimulated by a tactile stimulator, e.g., low level vibration at the shoulder of the patient. The third level is repeated up to a set number of times (x), which may vary from between 1 to about 5, in time intervals of between 1 and about 25 seconds (which may be a shortened period from the second level) depending on the condition of the patient, the type of sedation that the patient may be under and/or other factors. If the patient does not respond to at least a predetermined number of prompts by breathing when prompted (e.g., 50% or 60%, 70%, 80%, 90% or 100% of prompts given in the second level), the fourth level of the prompting protocol is initiated. If the patient has not resumed spontaneous breathing, the system will continue prompting at the third level. If the patient has resumed spontaneous breathing as detected by the patient sensors of the invention, the prompting protocol is exited until the system determines that the patient has reverted back to a condition of inadequate ventilation.

When the fourth level of the prompting protocol is initiated, the patient is again prompted to breathe with a verbal command using the patient's name at the higher decibel level, e.g., 80-100 dB and the patient is electrically stimulated. The electrical stimulation may start at approximately 10 mA and increase over time, such as in 10 mA increments every 10 seconds up to about 50 mA. The electrical stimulation is halted at the level at which the patient responds. The fourth level is repeated up to a set number of times (x), which may be only once, in a time interval of between 1 and about 25 seconds (which may be a shortened period from the third level) depending on the condition of the patient, the type of sedation that the patient may be under and/or other factors. If the patient does not respond, the patient requires immediate intervention from a healthcare provider, which may be an anesthesiologist, nurse or other clinician, to use both verbal and tactile stimuli. If the patient has not resumed spontaneous breathing, the system will continue prompting at the fourth level. If the patient has resumed spontaneous breathing as detected by the patient sensors of the invention, the prompting protocol is exited until the system determines that the patient has reverted back to a condition of inadequate ventilation.

The prompting protocol may also enter a continuous prompting mode where a given prompt is repeated immediately continuously until the SpO2 returns to above baseline level. If a continuous mode is maintained for a predetermined period of time, e.g., more than about 1-5 minutes and SpO2 drops below 85% for at least 10 seconds without any sufficient body motion, caretaker help may be immediately alerted by the system.

It should be noted that the verbal commands according the system of the invention may also be adjusted to reflect urgency in the voice if the patient fails to properly respond to initial or subsequent voice commands to breathe. In addition, the system of the invention may also include different voice intonations to better mimic the voice of a man, woman or child. In addition, the system may be able to record and use voice commands of a relative of the patient, such as a mother, father, sibling or guardian of which the patient may be familiar.

The system of the invention may also include a snooze function that will allow the system to be paused by a clinician to temporarily mute or stop breath prompting while the patient is being attended to, for patient trips to the restroom, for physical theory or other situations where temporary interruption of breath monitoring is necessary. In addition, the system of the invention may also display historical information about the number and frequency of system prompts to the patient and the patient's historical responses to such prompts. This allows the clinician to review the effectiveness of the system while the clinician has been away from the patient and to determine if adjustments to the system are warranted.

As previously noted, the system of the present invention may include a wired or wireless harness worn by the patient. As shown in FIG. 10, a patient worn harness, generally indicated at 100, includes a belt 102 that may be configured to wrap around a body portion of the patient, such as a wrist, and attach to itself at its ends as with hook and loop tape, a buckle or other devices known in the art. The belt 102 provides a support upon which the various components of the patient worn system are mounted. The patient worn harness 100 includes an accelerometer 104 for detecting patient movement, a pulse oximeter 106 for detecting the pulse of the patient and a thermometer 108 for detecting the temperature of the patient. In addition, an LED light 110 is provided to indicate the state of the patient worn system, e.g., on/off/alert. A buzzer 112 may provide vibration stimulation when prompted. A wireless communication module 114, such as a Bluetooth module, is also included for wireless communication with the monitoring system of the present invention. The system components are housed within a cover 116 that protects the various components of the patient worn system 100.

Accordingly, the present invention provides a ventilation sensor (respiratory rate, tidal volume or minute volume) and body motion input signals that are combined to initiate digitized verbal and tactile breath prompting. For example, input signal combinations may include:

The system of the present invention detects central vs. obstructive apnea and advises the clinician how to proceed (for example, apply CPAP or reduce opioid prescription).
  a) System searches for lack of effective breath detected (either central or obstructive apnea) and sufficient lack of body motion or hand motion.
  b) System searches for hypopnea and sufficient lack of motion or decreased SpO2
  c) System searches for airway obstruction
  d) System searches for combinations of a, b and c
  e) The conditions above may optionally be confirmed by decreased SpO2 from baseline levels SpO2 decreased from baseline levels means the SpO2 measured during the suspected ventilation problem is at least 3 points lower than the baseline level calculated at the beginning of the monitoring session and intermittently during the monitoring session when breath rate has been higher than 10 for at least three minutes. The intermittent measurements can be based on an average of the 3-10 SpO2 readings observed before an event or on an average SpO2 value for 10-30 seconds at selected intervals.

The system of the present invention detects central vs. obstructive apnea and advises the clinician how to proceed (for example, apply CPAP or reduce opioid prescription).

In addition system of the present invention personalizes the prompting stimulus to the particular patient's breath responsiveness in real time. That is, the response information is an input to the system, including stimulus escalation.

The system also uses a novel verbal and/or verbal and tactile approach to stimulating a patient to breathe where tactile stimulation may include body shake, limb shake, head tilt (via bladder that repeatedly elevates the head), electrical muscle tetany. Verbal prompts include the patient's name in phrases such as "Mr. Jones, take a deep breath," "Take a deep breath," "BREATHE!," "Mr. Jones, you need to take a deep breath," etc. In addition, the verbal prompting may be provided at different decibel levels that escalate from level to level where the levels may include: 1) Low voice, 2) Loud voice, 3) Loud voice with tactile stimulus, and 4) Loud voice, tactile stimulus and electrical muscle tetany.

A breath prompting protocol of the present invention includes respiratory rate (RR) and SpO2 measurements of the patient. A Baseline SpO2 is determined to be an average SpO2 over at least 10 seconds and at most 5 minutes while RR greater than or equal to 10. Nadir SpO2 equals the lowest SpO2 in the last 30 seconds that was not preceded by a step change down.

Prompting begins when no breath is detected for at least 30 seconds coupled with any SpO2 reading or RR<6 for at least 60 seconds, or RR<3 for at least 30 seconds and any SpO2 reading and little or no motion. Prompting also begins if SpO2<=89% for >3 seconds, SpO2 baseline >89% and there is little or no motion. A check that there is not a step change in SpO2 is also made. Prompting also begins if a change in SpO2>4% points from baseline within 3 min period and little or no motion is detected. Again, a check that there is not a step change in SpO2 is also made.

Prompting continues if a successful breath response is detected but no additional subsequent breaths occur within 12 seconds. Likewise, if the verbal prompting does not result in a breath detected by the patient monitors within 12 seconds, the verbal prompt will be repeated within 15 seconds, optionally accompanied by a shoulder shake from the shoulder massager.

Prompting ceases if SpO2 increases >4 percentage points from the nadir, SpO2 remains above 90% for >10 seconds, or there are at least 6 breaths per minute and any SpO2 during sufficient finger motion artifact or flat line.

An emergency rescue alert is initiated by the system if breath prompting is long-lasting (at least once per minute for more than 10 minutes) or breath prompting is ineffective (no breath response or SpO2 improvement subsequent to breath prompting).

It is contemplated, and will be apparent to those skilled in the art from the foregoing specification, drawings, and examples that modifications and/or changes may be made in the embodiments of the invention. Accordingly, it is expressly intended that the foregoing are only illustrative of preferred embodiments and modes of operation, not limiting thereto, and that the true spirit and scope of the present invention be determined by reference to the appended claims.

While the present invention has been described with reference to certain illustrative embodiments to illustrate what is believed to be the best mode of the invention, it is contemplated that upon review of the present invention, those of skill in the art will appreciate that various modifications and combinations may be made to the present embodiments without departing from the spirit and scope of the invention as recited in the claims. The claims provided herein are intended to cover such modifications and combinations and all equivalents thereof. Reference herein to specific details of the illustrated embodiments is by way of example and not by way of limitation.

Thus, aspects and applications of the invention presented here are described in the drawings and in the foregoing detailed description of the invention. Those of ordinary skill in the art will realize that the description of the present invention is illustrative only and not in any way limiting. Other embodiments of the invention will readily suggest themselves to such skilled persons including, without limitation, combinations of elements of the various embodiments. Various representative implementations of the present invention may be applied to any valve.

Unless specifically noted, it is intended that the words and phrases in the specification and the claims be given their plain, ordinary, and accustomed meaning to those of ordinary skill in the applicable arts. It is noted that the inventor can be his own lexicographer. The inventor expressly elects, as his own lexicographer, to use the plain and ordinary meaning of terms in the specification and claims unless they clearly state otherwise in which case, the inventor will set forth the "special" definition of that term and explain how it differs from the plain and ordinary meaning. Absent such statements of the application of a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of 35 U.S.C. § 112(f). Thus, the use of the words "function," "means" or "step" in the Detailed Description of the Invention or claims is not intended to somehow indicate a desire to invoke the special provisions of 35 U.S.C. § 112(f) to define the invention. To the contrary, if the provisions of 35 U.S.C. § 112(f) are sought to be invoked to define the inventions, the claims will specifically and expressly state the exact phrases "means for" or "step for" and the specific function (e.g., "means for heating"), without also reciting in such phrases any structure, material or act in support of the function. Thus, even when the claims recite a "means for . . . " or "step for . . . " if the claims also recite any structure, material or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

What is claimed is:

1. A system for prompting a patient experiencing ventilatory depression to breathe, comprising:
   at least one breath sensor configured to detect whether a patient is sufficiently breathing and generating breath sensor data indicative of the patient's breathing;
   a breath prompting protocol system, the breath prompting protocol system activated if the breath sensor data indicates that the patient is not sufficiently breathing, the breath prompting protocol system configured to generate an audible prompt for the patient to breath using a recorded voice, determine from the breath sensor data if the patient responded to the audible prompt by taking at least one breath in response thereto, and repeat the audible prompt if the patient failed to respond to the audible prompt;
   at least one motion sensor to detect movement of at least one body part of the patient, the breath prompting protocol system configured to disregard the breath sensor data if the at least one motion sensor detects that the patient is moving.

2. The system of claim 1, wherein the at least one breath sensor is configured to measure at least one of intranasal pressure, intraoral pressure, mouth expiration pressure, expired CO2, changes in airway humidity, temperature at the mouth or nostrils, sound or vibration at the nose, mouth or larynx, photoplethysmography, radio frequency, Wi-Fi modulation or chest impedance.

3. The system of claim 1, wherein the at least one motion sensor comprises an accelerometer or a gyroscope.

4. The system of claim 1, wherein the breath prompting protocol system increases a sound level of the audible prompt if the breath sensor data indicates inadequate breathing after the audible prompt.

5. The system of claim 4, further comprising a tactile stimulator coupled to the patient, the breath prompting protocol system activating the tactile stimulator and the audible prompt at the increased sound level if the breath sensor data indicates inadequate breathing after the audible prompt alone at the increased sound level.

6. The system of claim 5, further comprising an electrical stimulator coupled to the patient, the breath prompting protocol system activating the electrical stimulator and the audible prompt at the increased sound level if the breath sensor data indicates inadequate breathing after generating the audible prompt at the increased sound level and activation of the tactile stimulator to the patient.

7. The system of claim 6, further comprising a SpO2 sensor for detecting a SpO2 level of the patient.

8. The system of claim 7, wherein the breath prompting protocol system maintains a level of prompting if the SpO2 level of the patient is adequate but the patient is not adequately responding to the audible prompt or tactile stimulation.

9. The system of claim 7, wherein the prompting protocol system increases a level of prompting if the SpO2 level drops below a predetermined level.

10. The system of claim 9, wherein the predetermined level of the SpO2 is approximately 85% for at least 10 seconds.

11. The system of claim 1, wherein the breath prompting protocol system stops audible prompts if the breath sensor data indicates that the patient is spontaneously breathing.

12. The system of claim 1, further comprising an alert system for alerting a care provider in the event that the prompting protocol system is unsuccessful in prompting the patient to breathe after a predetermined number of audible prompts.

13. The system of claim 1, further comprising a breathing assessment system configured to determine a ventilation problem type of the patient from the breath sensor data if the breath sensor data indicates that the patient is not adequately breathing.

14. The system of claim 13, wherein the breathing assessment system is configured to determine if the ventilation problem is at least one of central apnea, partial airway obstruction, complete airway apnea, ventilatory depression or combinations thereof.

15. The system of claim 14, further comprising a monitor configured to display the ventilation problem, breath sensor data and breath prompting protocol status.

16. A system for prompting a patient experiencing ventilatory depression to breathe, comprising:
   at least one breath sensor for detecting ventilatory depression of a patient;
   at least one motion sensor for detecting a sufficient lack of motion of the patient to indicate that the patient may be unconscious; and
   a computer-based monitoring system having a processor receiving signals from the at least one breath sensor and at least one motion sensor to determine whether the patient is experiencing ventilatory depression; and
   a breath prompting system configured to provide verbal and tactile prompting to the patient in increasing intensity of at least one of the verbal and tactile prompting if the patient is experiencing ventilatory depression to attempt to improve patient ventilation, the breath prompting system configured to not provide verbal and tactile prompting to the patient if the at least one motion sensor detects that the patient is moving.

17. The system of claim 16, wherein the monitoring system utilizes data from the at least one breath sensor to determine a ventilation problem type of the patient.

18. The system of claim 17, wherein the monitoring system is configured to determine the ventilation problem from the group consisting of central apnea, partial airway obstruction, complete airway apnea, ventilatory depression or a combination thereof.

19. The system of claim 17, wherein the monitoring system further comprises a display monitor to display the ventilation problem type on the monitor.

20. The system of claim 16, wherein the monitoring system is configured to determine a level of prompting required to achieve a breath response of the patient.

21. A system for prompting a patient experiencing ventilatory depression to breathe, comprising:
at least one breath sensor configured to detect whether a patient is sufficiently breathing and generating breath sensor data indicative of the patient's breathing;
a breath prompting protocol system, the breath prompting protocol system activated if the breath sensor data indicates that the patient is not sufficiently breathing, the breath prompting protocol system configured to generate an audible prompt for the patient to breath using a recorded voice, determine from the breath sensor data if the patient responded to the audible prompt by taking at least one breath in response thereto, and repeat the audible prompt if the patient failed to respond to the audible prompt, the breath prompting protocol system increasing a sound level of the audible prompt if the breath sensor data indicates inadequate breathing after the audible prompt;
a tactile stimulator configured to be coupled to the patient and produce a tactile stimulation to the patient, the breath prompting protocol system activating the tactile stimulator and the audible prompt at the increased sound level if the breath sensor data indicates inadequate breathing after the audible prompt alone at the increased sound level; and
a SpO2 sensor for detecting a SpO2 level of the patient, the breath prompting protocol system configured to maintain a level of prompting if the SpO2 level of the patient is adequate but the patient is not adequately responding to the audible prompt or tactile stimulation or increase the level of prompting if the SpO2 level drops below a predetermined level.

22. The system of claim 21, further comprising an electrical stimulator, the breath prompting protocol system activating the electrical stimulator, the audible prompt at the increased sound level and the tactile stimulator if the breath sensor data indicates inadequate breathing after activation of the audible prompt at the increased sound level and the tactile stimulation.

23. The system of claim 21, further comprising at least one motion sensor to detect movement of at least one body part of the patient.

24. The system of claim 23, wherein the at least one motion sensor comprises an accelerometer or a gyroscope.

25. The system of claim 23, wherein the breath prompting protocol system disregards the breath sensor data if the at least one motion sensor detects that the patient is moving.

26. The system of claim 21, wherein the at least one breath sensor is configured to measure at least one of intranasal pressure, intraoral pressure, mouth expiration pressure, expired CO2, changes in airway humidity, temperature at the mouth or nostrils, sound or vibration at the nose, mouth or larynx, photoplethysmography, radio frequency, Wi-Fi modulation or chest impedance.

27. The system of claim 26, wherein the monitoring system utilizes data from the breath sensor to determine a ventilation problem type of the patient.

28. The system of claim 21, further comprising a breathing assessment system configured to determine a ventilation problem type of the patient from the breath sensor data if the breath sensor data indicates that the patient is not adequately breathing, wherein the ventilation problem is at least one of central apnea, partial airway obstruction, complete airway apnea, ventilatory depression or a combination thereof.

* * * * *